United States Patent [19]

Cullen et al.

[11] Patent Number: 4,956,283

[45] Date of Patent: Sep. 11, 1990

[54] PROCESS FOR PREPARING MACROLIDE ANTIBIOTICS BY CULTURING STREPTOMYCES HIRSUTUS ATCC 53513

[75] Inventors: Walter P. Cullen; James R. Hauske; Hiroshi Maeda; Junsuke Tone, all of New York, N.Y.

[73] Assignee: Pfizer Inc., New York, N.Y.

[21] Appl. No.: 322,149

[22] Filed: Mar. 10, 1989

Related U.S. Application Data

[62] Division of Ser. No. 938,219, Dec. 5, 1986, Pat. No. 4,835,141.

[51] Int. Cl.$^5$ .............................................. C12P 19/62
[52] U.S. Cl. .................................... 435/76; 435/886; 536/7.1
[58] Field of Search ................... 536/7.1; 435/886, 76

[56] References Cited

U.S. PATENT DOCUMENTS 3,868,464  2/1975  Koaze et al. ................... 435/95
4,543,334  9/1985  Celmer et al. .................. 336/7.1

OTHER PUBLICATIONS

The Merck Index, 10th Edition, Merck & Co., Inc., Rahway, N.J., 1983, Abstract No. 1990.
Journal of Organic Chemistry, vol. 51, pp. 2808-2814, (1986).

Primary Examiner—Johnnie R. Brown
Assistant Examiner—Elli Peselev
Attorney, Agent, or Firm—Peter C. Richardson; J. Trevor Lumb; Gregg C. Benson

[57] ABSTRACT

An antibiotic complex, containing three major components, has been isolated from fermentations of a new strain of the microorganism *Streptomyces hirautus*. The major components are new, neutral, macrolide antibiotic compounds, which are useful as antibacterial agents against certain gram-positive bacteria.

4 Claims, No Drawings

PROCESS FOR PREPARING MACROLIDE ANTIBIOTICS BY CULTURING STREPTOMYCES HIRSUTUS ATCC 53513

CROSS-REFERENCE TO RELATED APPLICATION

This application is a division of application Ser. No. 06/938,219, filed Dec. 5, 1986, now U.S. Pat. No. 4,835,141.

BACKGROUND OF THE INVENTION

This invention relates to a new antibiotic complex which has been isolated by fermentation of a new strain of the microorganism *Streptomyces hirsutus*. The new antibiotic complex has been designated CP-61,884, and it has been shown to contain three major components. Chemically, these major components are new members of the macrolide class of antibiotics.

The three major components of antibiotic complex CP-61,884 are neutral macrolides, containing a 16-membered lactone ring, and they can be compared to chalcomycin. See further, The Merck Index, 10th Edition, Merck & Co., Inc., Rahway, New Jersey, U.S.A., 1983, Abstract No. 1990 (page 283).

SUMMARY OF THE INVENTION

This invention provides new macrolide antibiotic compounds selected from the group consisting of

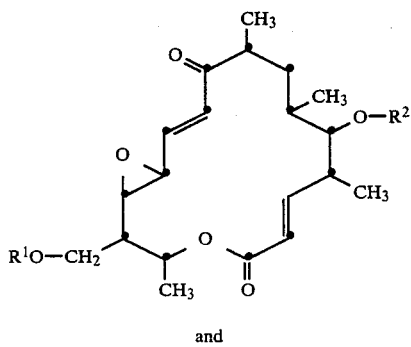

and

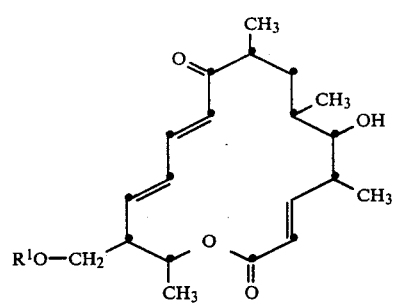

wherein $R^1$ is the radical of the formula

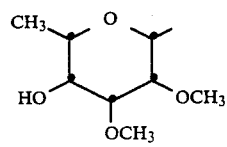

and $R^2$ is a radical selected from the group consisting of

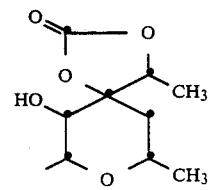

and

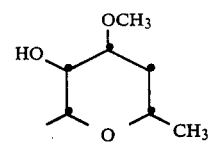

The macrolide compounds of the formulas I and II have been isolated from fermentations of a new strains of the microorganism *Streptomyces hirsutus*, and said compounds are antibacterially-active against certain gram-positive bacteria. The new strain of *Streptomyces hirsutus* was initially designated N521-25, and it is now on deposit with the American Type Culture Collection under Accession No. 53513.

Accordingly, also included within this invention are: a method of treating a bacterial infection in a mammalian subject using a compound of formula I or II; pharmaceutical compositions which comprise a compound of the formula I or II and a pharmaceutically-acceptable carrier; a process for preparing a compound of the formula I or II by fermentation of *Streptomyces hirsutus* ATCC 53513, or a mutant thereof having the ability to produce a compound of formula I or II; and a biologically-pure culture of *Streptomyces hirsutus* ATCC 53513, or a mutant thereof having the ability to produce a compound of formula I or II.

The preferred macrolide antibiotic of this invention is the compound of formula I, wherein $R^1$ is of formula III and $R^2$ is of formula V.

DETAILED DESCRIPTION OF THE INVENTION

The compounds of formulas I and II are the three major components of a new antibiotic complex which has been obtained by fermentations of a new microorganism of the genus Streptomyces. The new microorganism was isolated from a soil sample collected from a woodland in Sacramento, California, and it was designated initially as culture N521-25. Subsequently, it was characterized and identified by Liang H. Huang, Ph.D., Pfizer Inc., Groton, Connecticut, as described herein below. Culture N521-25 was shown thereby to be a new strain of *Streptomyces hirsutus*.

Culture N521-25 was found to produce narrow hyphae of the Actinomycetales, spore chains produced on the aerial mycelium and an unfragmented substrate mycelium, characteristic of the genus Streptomyces.

Culture N521-25 was planted from a slant into liquid, ATCC medium No. 172 and grown for four days at 28° C. on a shaker. It was then centrifuged for 20 minutes, washed three times with sterile distilled water and planted onto media commonly used for identification of members of the Actinomycetales. The cultures were incubated at 28° C. and results were read at appropriate times, most-commonly at 14 days. Specific identification media used for the characterization of culture N521-25, and references for their composition, are as follows:

1. Tryptone Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Czapek-Sucrose Agar—S. A. Waksman, The Actinomycetes, Vol. 2, medium no. 1, p. 328, 1961.
7. Glucose-Asparagine Agar—Ibid, medium no. 2, p. 328.
8. Bennett's Agar—Ibid, medium no. 30, p. 331.
9. Emerson's Agar—Ibid, medium no. 28, p. 330.
10. Nutrient Agar—Ibid, medium no. 14, p. 330.
11. Peptone-Yeast Extract Iron Agar - (ISP #6 medium, Difco).
12. Gordon and Smith's Tyrosine Agar—R. E. Gordon and M. M. Smith, J. Bacteriol. 69: 147-150, 1955.
13. Casein Agar—Ibid.
14. Calcium Malate Agar—S. A. Waksman, Bacteriol. Rev. 21: 1-29, 1957.
15. Gelatin—R. E. Gordon and J. M. Mihm, J. Bacteriol. 73: 15-27, 1957.
16. Starch—Ibid.
17. Organic Nitrate Broth—Ibid.
18. Dextros Nitrate Broth—S. A. Waksman, The Actinomycetes, Vol. 2, medium no. 1, p. 328, 1961, with 3 g dextrose substituted for 30 g sucrose and agar omitted.
19. Potato Carrot Agar—M. P. Lechevalier, J. Lab. and Clin. Med. 71: 934-944, 1968, but use only 30 g potatoes, 2.5 g carrot and 20 g agar.
20. 2% Tap Water Agar.
21. Skim Milk—Difco.
22. Cellulose utilization —(a)
    H. L. Jensen, Proc. Linn. Soc. N.S.W. 55: 231-248, 1930.
    (b) M. Levine and H. W. Schoenlein, A Compilation of Culture Media, medium no. 2511, 1930.
23. Carbohydrates—ISP #9 medium, Difco.
24. Temperature Range—ATCC medium 196 in ATCC Media Handbook 1st ed., p. 11, 1984.

Culture N521-25 exhibited the following characteristics, with colors being given in common terminology and also with reference to color chips from the *Color Harmony Manual*, 4th Edition. The methods of whole cell amino acid and sugar analyses were those described in Becker, B. et al., Appl. Microbiol. 12: 421-423, 1964; and in Lechevalier, M. P., J. Lab. Clin. Med., 71: 934-944, 1968.

Yeast Extract-Malt Extract Agar—Growth good, white, cream to blue (2ca, near gray series 22dc, 24fe); raised, granular to wrinkled, with white to white-blue aerial mycelium; reversed yellowish to yellowish-brown (21c, 31c, 31e); no soluble pigment.

Oatmeal Agar—Growth poor to moderate, pale gray to pale green-gray to cream (2ca, near gray series 1dc, 24½dc, 24dc, 24fe); slightly raised to raised, smooth to granular, or appearing as isolated colonies; aerial mycelium pale gray to pale green-gray; reverse pale gray to cream (near gray series 2bc, 2ca); no soluble pigment.

Inorganic Salts-Starch Agar—Growth moderate to good, cream, yellowish, yellowish brown to green-gray (2ca, 3ea, 31c, near gray series 24fe, 24½fe); slightly raised, smooth, or granular in some areas; aerial mycelium green-gray; reverse cream, yellowish brown to green-gray (2ca, 3ic, near gray series 24fe); no soluble pigment.

Glycerol-Asparagine Agar—Growth good, white, pale yellow-orange, gray to green-gray (3ea, near gray series 1fe, 24½fe); raised, granular, or slightly wrinkled; aerial mycelium same as surface; reverse pale gray, yellowish to brown (near gray series 1dc, 21c, 31g); soluble pigment cream (2ca).

Czapek-Sucrose Agar—Growth moderate, pale green-gray, pale gray to gray (near gray series 24½dc, 2dc, 2fe, 2ih); thin to slightly raised, smooth to granular; aerial mycelium same as surface; reverse pale gray to gray (near gray series 2dc, 2fe); no soluble pigment.

Glucose-Asparagine Agar—Growth poor to moderate, cream (2ca), slightly raised; appearing as isolated, small colonies; aerial mycelium lacking; reverse cream (2ca); no soluble pigment.

Gordon and Smith's Tyrosine Agar—Growth moderate to good, green-gray with black sectors (near gray series 24½ih, 24ih, 24ml), slightly raised, smooth; aerial mycelium same as surface; reverse gray to green-gray (near gray series 1fe, 24½fe); soluble pigment pale yellowish (2ea).

Calcium Malate Agar—Growth moderate, white, pale pink to dark gray (4ca, near gray series 1ih, 1ml); thin or raised, smooth or granular; aerial mycelium same as surface; reverse pink to gray (5ca, near gray series 2fe); no soluble pigment.

Casein Agar—Growth good, brown to dark brown (4ie, 41g), moderately raised, wrinkled or granular, with sectors of white aerial mycelium; reverse same as surface; soluble pigment brown (41c).

Bennett's Agar—Growth good, white, cream to orange (2ca, 4ia, 41c); moderately raised, slightly wrinkled, with white aerial mycelium; reverse cream to yellowish (2ca, 3ga); no soluble pigment.

Emerson's Agar—Growth good, white to green-gray (near gray series 24½fe, 24½ih, 24ih), raised, wrinkled; aerial mycelium same as surface; reverse yellowish brown to brown (41c, 31e); soluble pigment yellowish brown (31c).

Nutrient Agar—Growth moderate to good, white to cream (2ca), moderately raised, smooth or slightly granular, with white aerial mycelium; reverse cream to pale yellowish (2ca, 2ea); no soluble pigment.

Gelatin Agar—Growth good, pale green-gray (near gray series 24½dc, 24dc, 24fe) with a cream to red-purple edge (2ca, 6½ie), moderately raised, wrinkled or granular but smooth toward the edge, with pale green-gray aerial mycelium; reverse cream to brown (2ca, 41e, 41g); no soluble pigment.

Starch Agar—Growth good, white, green-gray to brown (near gray series 24fe, 24ih, 4ng) with a cream (2ca) edge; raised, wrinkled, with white to green-gray aerial mycelium; reverse brown (4ng, 4ne); no soluble pigment.

Potato Carrot Agar—Growth moderate, green-gray (near gray series 24½fe, 24½ih), slightly raised, smooth or granular, with green-gray aerial mycelium; reverse same as surface; no soluble pigment.

Tap Water Agar—Growth poor to moderate, green-gray (near gray series 24½fe, 24½ih), thin to slightly raised, smooth, with green-gray aerial mycelium; reverse same as surface; no soluble pigment.

Morphological Properties—The morphological properties were observed on inorganic salts-starch agar after 14 days of incubation; spore mass in the Green-color series; spore chains in Section Rectiflexibiles, straight, flexuous, wavy to hooked; short, 4 to 12 spores per spore chain; sporophores monopodially or verticillately branched; spores globose, oval to elliptical, 1.2–1.8 micrometer in diameter or 1.2–1.8 (−2.4)×1.2–1.4 (−1.8) micrometer; spiny, as revealed by scanning electron microscopy.

Biochemical Properties—Melanin not produced; hydrogen sulfide produced; gelatin liquefied; starch hydrolyzed; nitrate not reduced to nitrite; growth but no decomposition on both cellulose broths; coagulation and clearing on milk; casein digestion positive; calcium malate digestion positive; tyrosine digestion positive. Carbohydrate utilization; glucose, arabinose, fructose, inositiol, mannitol, raffinose, rhamnose, sucrose, and xylose all utilized.

Cell-Wall Analyses—The whole-cell hydrolyzates were found to contain LL-diaminopimelic acid and glucose.

The relationship of temperature to growth rate for culture N521-25 was as follows: 21° C., moderate to good growth; 28° C., good growth; 37° C., moderate growth; and 45° C., poor growth.

The culture N521-25 is characterized by the negative melanin reaction, the green-gray aerial mycelium, the straight to flexuous spore chains, and the spores with a spiny surface. The whole-cell hydrolysates reveal the presence of LL-diaminopimelic acid and the absence of diagnostic sugars. The culture utilizes glucose, arabinose, fructose, inositol, mannitol, raffinose, rhamnose, sucrose and xylose. Compared with the known species of Streptomyces, it closely resembles *S. hirsutus*. Thus, *S. hirsutus* ATCC 19773 was grown side-by-side and compared with culture N521-25.

Except for its inability to reduce nitrate to nitrite, the culture N521-25 agrees with *S. hirsutus* in all of the other biochemical properties as well as in the temperature relations. Both cultures share the same morphological properties and most of the cultural properties. A few cultural differences were noted, however. The culture N521-25 but not *S. hirsutus* may produce yellowish brown substrate mycelium on yeast extract-malt extract agar, inorganic salts-starch agar and glycerol-asparagine agar. In the culture N521-25, more aerial mycelium is produced on glycerol-asparagine agar, Czapek-sucrose agar and tyrosine agar. On some media such as inorganic salts-starch agar, Emerson's agar, potato carrot agar, and tap water agar, the aerial mycelium of the culture N521-25 shows slightly more greenish tint in the green-gray background than that of *S. hirsutus*. On Bennett's agar and casein agar, the colonies of the culture N521-25 are cream to orange and brown to dark brown, respectively, but those of *S. hirsutus* are cream. These cultural differences are considered as minor and it is concluded that the culture N521-25 represents a new strain of *Streptomyces hirsutus* Ettlinger, Corbaz and Hutter.

Culture N521-25 was deposited with the American Type Culture Collection ("ATCC"), 12301 Parklawn Drive, Rockville, Md. 20852, U.S.A. under the provisions of the Budapest Treaty on July 1, 1986, under Accession No. ATCC 53513. All restrictions on the availability of *Streptomyces hirsutus* ATCC 53513 will be irrevocably removed not later than the date of issuance of a patent on this application. Additionally, the permanancy of the deposit is guaranteed throughout the life of the patent or for 30 years from the date of deposit, whichever is longer.

The antibiotic complex of this invention can be obtained by fermenting the microorganism *Streptomyces hirsutus* ATCC 53513 under submerged aerobic conditions, followed by extraction of the complex from the fermentation broth. The compounds of formulas I and II can be obtained from the complex by classical methods such as chromatography or counter-current distribution. Moreover, a compound of formula I or II can be obtained by fermentation of a mutant of *S. hirsutus* ATCC 53513 having the ability to produce a compound of formula I or II. Mutants of *S. hirsutus* ATCC 53513 can be obtained by standard techniques and they can arise naturally as a result of spontaneous mutations.

Fermentation of *S. hirsutus* ATCC 53513 or a mutant thereof can be carried out in a manner similar to that described in U.S. Pat. No. 4,411,892 for fermentation of *Streptomyces albus* subsp. indicus ATCC 39012. In general, the *S. hirsutus* can be grown from 24° to 36° C. under submerged conditions in an aqueous nutrient medium, with aeration and agitation. Suitable nutrient media contain an assimilable carbohydrate source, such as a sugar, starch or glycerol; organic nitrogen substances, such as soybean mean, casamino acids or yeast extract; growth substances, such as grain solubles, fish meal or cotton seed meal; mineral salts containing trace elements, such as iron, cobalt, copper and zinc; and calcium carbonate and/or phosphates as buffering agents.

Inoculum is prepared by scraping vegetative cells from slants or Roux bottles inoculated with *Streptomyces hirsutus* ATCC 53513 or a mutant thereof. A solid medium suitable for initial growth on slants and Roux bottles is ATCC medium No. 172, which has the following composition.

| ATCC 172 | |
|---|---|
| Ingredient | Amount (gms./liter) |
| Glucose | 10 |
| Soluble Starch | 20 |
| Yeast Extract | 5 |
| NZ Amine A (Humko)* | 5 |
| Calcium Carbonate | 1 |
| Distilled Water to 1000 ml.; ph to 7.0 with KOH | |
| Add Agar | 20 |

*A purified enzymatic digest of casein.

Vegetative cells from slants are used to inoculate either shake flasks or inoculum tanks. Alternately the inoculum tanks are inoculated from shake flasks. In shake flasks, growth will generally have reached its maximum in 96 to 120 hours, whereas in the inoculum tanks growth will usually be at the most favorable period in 72 to 96 hours after inoculation. A fermentor is inoculated with vegetative broth from the inoculum flask or tank under completely aseptic conditions, and fermented for a period of 48 to 120 hours. Aeration is maintained in the shake flask by agitation on a shaker or in tanks by forcing sterile air through a sparger at the rate of ½ to 2 volumes of air per volume of broth per minute. The speed of agitation (stirring) depends upon the type of agitator employed; a shake flask is usually run at 150 to 200 cycles per minute and a fermentor at 300 to 1700 revolutions per minute. Sterility is maintained at all times. The temperature is regulated between 28° and 36° C. Foaming can be controlled using sterile antifoaming agents, such as refined soybean oil.

Shake flasks are prepared using one of the following media:

| CL13NZ | | JDYTT | |
|---|---|---|---|
| Ingredient | Grams/liter | Ingredient | Grams/liter |
| Glucose | 20 | Cerelose | 10 |
| Soy Flour | 10 | Corn Starch | 5 |
| NZ Amine YTT* | 5 | Corn Steep Liquor | 5 |
| Sodium Sulfate | 0.5 | NZ Amine YTT* | 5 |
| Cobalt Chloride | 0.002 | Cobalt Chloride | 0.002 |
| Calcium Carbonate | 2 | Calcium Carbonate | 3 |
| Water to 1 liter; ph 6.9–7.0 | | Water to 1 liter; ph 6.9–7.0 | |

*An enzymatic digest of casein.

One hundred milliliters of medium is distributed into 300 ml shake flasks and sterilized at 120° C. and 15 p.s.i. for 30 minutes. After cooling, the medium is inoculated with a vegetative cell suspension from the *Streptomyces hirsutus* grown on ATCC 172 medium in agar. The flasks are shaken at 28° C. on a rotary shaker having a displacement of 1.5 to 2.5 inches and 150 to 200 cycles per minute (CPM) for three to four days. One flask is used to inoculate a five liter fermentation vessel containing three liters of CL13NZ, JDYTT or the following medium:

| CN-2 | |
|---|---|
| Ingredient | Grams/liter |
| Cerelose | 10 |
| Corn Starch | 10 |
| Soybean Flour | 10 |
| NZ Amine YTT* | 10 |
| Cobalt Chloride | 0.002 |
| Calcium Carbonate | 1 |
| Water to 1 liter; ph 6.9–7.0 | |

*An enzymatic digest of casein.

One milliliter of L61 silicone is added as an antifoaming agent, then the vessels are sealed and sterilized at 120° C. and 15 p.s.i. for 45 minutes. The pots are inoculated with one (ca 3% inoculum) flask, fermented for 96 to 144 hours at 30° C., stirred at 1700 revolutions per minute (RPM) with an air rate of one volume of air per volume of liquid per minute. When the fermentation is complete (based on an antibiotic disc assay using *Staphylococus aureus* ATCC 6538), the fermentors are stopped and extracted twice with one-third to one-half volume of a solvent, such as methyl isobutyl ketone or n-butanol. The solvent layer is separated from the aqueous phase by aspiration or centrifugation, sparkled, and concentrated in vacuo to a viscous oil.

The progress of antibiotic production during fermentation, and the bioactivity of the fermentation broth and recovery streams, can be monitored by biological assay of the broth employing a sensitive strain of *Micrococcus luteus* (e.g., ATCC 9341) or *Staphylococcus aureus* (e.g., ATCC 6538). The components in the broth and recovery streams can be visualized by thin-layer chromatography (tlc) using Analtech silica 9el GF plates in ethyl acetate or chloroform/methanol(9:1). The developed plates are sprayed with vanillin reagent (3 g vanillin in 75 ml ethanol and 25 ml 85% phosphoric acid) and heated to 80° C. The antibiotics of this invention appear as greyish/blue spots. The developed tlc plate can also be overlayed with agar, seeded with either *S. aureus* or *M. luteus* to which tetrazolium dye has been added, and incubated at 37° C. for 16 hours to visualize the antibiotics (white against a pink background).

The antibiotic complex of this invention can be isolated after fermentation of *Streptomyces hirsutus* ATCC 53513, or a mutant thereof, by extraction of the whole broth at natural pH with a volatile, organic solvent, such as n-butanol, methyl isobutyl ketone or chloroform. Evaporation of the organic solvent then affords a syrup, from which the antibiotic complex, and ultimately the individual components thereof, can be recovered by repeated chromatography, especially using silica gel. Alternatively the whole broth can be filtered to remove the mycelium, and then the filtrate is extracted, evaporated and chromatographed.

The antibiotic complex of this invention, and the individual components thereof of formulas I and II, possess antibacterial activity against certain gram-positive bacteria. This antibacterial activity can be demonstrated by measuring the minimum inhibitory concentration (MIC) of the complex, or individual component thereof, against a variety of organisms, according to standard procedures. Thus, the MIC's can be measured by the procedure recommended by the International Collaborative Study on Antibiotic Sensitivity Testing (Ericcson and Sherris, *Acta Pathologica et Microbiologia Scandinav*, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 50 mcg./ml. Single colonies are disregarded when reading plates after 18 hours at 37° C. The susceptibility (MIC) of the test organism is accepted as the lowest concentration of compound capable of producing complete inhibition of growth as judged by the unaided eye. In particular the compounds of formulas I and II are antibacterially-active against certain strains of *Staphylococcus aureus* and *Staphylococcus epidermidis*.

The antibacterial activity of the antibiotic complex of the invention, and the individual components of formulas I and II, makes them valuable for the treatment of bacterial infections caused by susceptible organisms in mammalian subjects, e.g., humans.

When using an antibacterial compound of this invention in a mammal, the compound can be administered either alone, or in admixture with other antibiotic substances and/or pharmaceutically-acceptable carriers or diluents. Said carrier or diluent is chosen on the basis of the intended mode of administration. For example, when considering an oral mode of administration, an antibacterial compound of this invention can be used in the form of syrups, elixirs, aqueous solutions and suspensions, and the like, in accordance with standard pharmaceutical practice. The proportional ratio of active ingredient to carrier will naturally depend on the dosage contemplated; however, said proportional ratio will normally be in the range from 2:1 to 1:5 by weight, and preferably 1:1 to 1:4. An antibacterial compound of this invention can also be administered parenterally, which includes intramuscular, intraperitoneal, subcutaneous and intravenous administration. For these purposes, sterile solutions of the active ingredient are usually prepared, and the pH of the solutions are suitably adjusted and buffered. For intravenous use, the total concentration of solutes should be controlled to render the preparation isotonic.

When a compound of the formula I or II is used to treat a bacterial infection in a mammalian subject, an antibacterially-effective amount will be used. Such an amount will not differ significantly from the dosages usually used for other macrolide antibiotics. In general, the prescribing physician or veterinarian will determine the appropriate dosage for a given host, and this will vary according to weight and response of the individual host, as well as the nature and severity of the host's symptoms and the virulence of the invading microorganism. However, in human subjects, the compounds of formula I and II will normally be used orally at dosages in the range from about 20 to about 50 milligrams per kilogram of body weight per day, and parenterally at dosages from about 10 to about 30 milligrams per kilogram of body weight per day, usually in divided dosages.

The following example is provided solely for further illustration.

EXAMPLE I

Fermentation of Streptomyces hirsutus ATCC 53513.

Scale-up in large fermentors was carried out by preparing shake flasks containing 0.7 liters of CL13NZ or JDYTT medium. The shake flask inoculum was fermented for 3 to 5 days at 28° C., and used to inoculate a 50 gallon fermentor containing 25 gallons of JDYTT medium. Approximately one liter of inoculum was used in the tank. The fermentor, after running 5 to 7 days, was harvested (ca. 25 gallons). The whole broth was extracted with 1/5 volume of methyl isobutyl ketone at natural pH, separated on an alpha DeLaval LAPX separator and the solvent was concentrated in vacuo to an oil. The oil was further concentrated on a cyclone evaporator to a syrup. The syrup was suspended in heptane to remove the oils, and then it was filtered through a bed of filter aide and washed repeatedly with heptane. The antibiotic complex was dissolved in chloroform, and then it was chromatographed on a silica gel column. The column was eluted sequentially with chloroform, chloroform/ethyl acetate, ethyl acetate, acetone and lastly methanol. The elution was followed by thin layer chromatography and bioassay of the fractions. The active cuts were combined, concentrated, dissolved in chloroform and rechromatographed on 150 g of Woelm alumina to give a purified solid. Additional separations were performed on LH20 sephadex in methanol, followed by chromatography by HPLC on a Waters Prep 500A silica gel column using ethyl acetate. Finally, preparative thin-layer chromatography yielded the individual antibiotics of formulas I and II.

The $^{13}C$ nuclear magnetic resonance spectrum (CDCl$_3$ solution, 62.5 MHz) of the compound of the formula I, wherein R$^1$ is formula III and R$^2$ is formula V, showed absorptions at 200.95, 165.39, 151.21, 143.96, 125.60, 120.55, 103.44, 100.93, 86.96, 81.92, 80.52, 79.69, 75.11, 72.74, 70.71, 68.70, 67.82, 67.04, 61.69, 59.65, 59.04, 58.91, 56.81, 49.48, 44.68, 41.78, 36.85, 34.14, 32.02, 20.91, 18.75, 18.41, 17.78, 17.58 and 17.01 ppm, downfield from tetramethylsilane. On combustion analysis, this compound afforded the following results: C,61.27; H,8.19% (Calcd. for $C_{35}H_{56}O_{13}$: C,61.40; H,8.23%).

We claim:

1. A process for preparing a macrolide antibiotic compound selected from the group consisting of

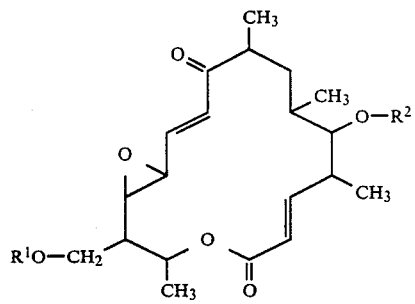

and

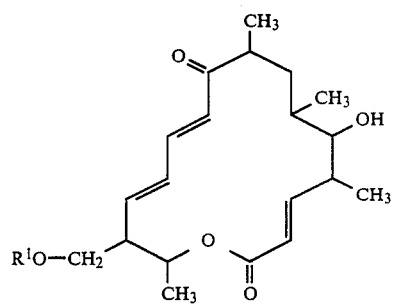

wherein R$^1$ is the radical of the formula

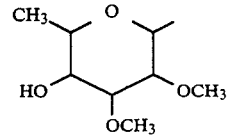

and R$^2$ is a radical selected from the group consisting of

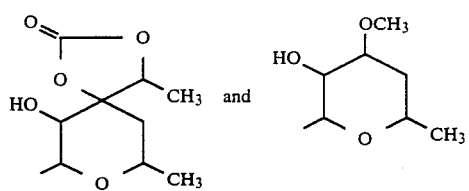

which comprises cultivating the microorganism *Streptomyces hirsutus* ATCC 53513 or a mutant thereof having the ability to produce a macrolide antibiotic compound selected from said group, in an aqueous culture medium containing assimilable sources of carbon, nitrogen and inorganic salts, under submerged, aerobic conditions, until a recoverable amount of a macrolide antibiotic compound selected from said group is obtained.

2. The process according to claim 1, which comprises cultivating the microorganism *Streptomyces hirsutus* ATCC 53513 in an aqueous culture medium containing assimilable sources of carbon, nitrogen and inorganic salts, under submerged, aerobic conditions, until a recoverable amount of a macrolide antibiotic compound according to claim 1 is obtained.

3. A biologically-pure culture of the microorganism *Streptomyces hirsutus* ATCC 53513 or a mutant thereof, said microorganism or mutant thereof having the ability to produce a macrolide antibiotic compound according to claim 1, in recoverable quantity, upon cultivation in an aqueous culture medium containing assimilable sources of carbon, nitrogen and inorganic salts.

4. A biologically-pure culture of the microorganism *Streptomyces hirsutus* ATCC 53513, according to claim 3.

* * * * *